(12) United States Patent
Choi et al.

(10) Patent No.: US 11,147,521 B2
(45) Date of Patent: Oct. 19, 2021

(54) APPARATUS AND METHOD FOR HEALTH CARE

(71) Applicant: SAMSUNG ELECTRONICS CO., LTD., Suwon-si (KR)

(72) Inventors: Ka Ram Choi, Hwaseong-si (KR); Sang Kon Bae, Seongnam-si (KR); So Young Lee, Daejeon (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 285 days.

(21) Appl. No.: 16/415,079

(22) Filed: May 17, 2019

(65) Prior Publication Data
US 2020/0077961 A1 Mar. 12, 2020

(30) Foreign Application Priority Data
Sep. 11, 2018 (KR) .................. 10-2018-0108141

(51) Int. Cl.
A61B 5/00 (2006.01)
A61B 5/0205 (2006.01)
(Continued)

(52) U.S. Cl.
CPC ........ A61B 5/7278 (2013.01); A61B 5/02055 (2013.01); A61B 5/486 (2013.01); A61B 5/6843 (2013.01); A61B 5/7285 (2013.01); A61B 5/0075 (2013.01); A61B 5/021 (2013.01); A61B 5/026 (2013.01); A61B 5/02007 (2013.01);
(Continued)

(58) Field of Classification Search
CPC ..... A61B 5/7278; A61B 5/2055; A61B 5/486; A61B 5/6843
See application file for complete search history.

(56) References Cited

U.S. PATENT DOCUMENTS 6,923,763 B1 * 8/2005 Kovatchev ............ G16H 40/67
600/300
6,990,364 B2 1/2006 Ruchti et al.
(Continued)

FOREIGN PATENT DOCUMENTS

CN 106343979 A 1/2017
JP 2009-039267 A 2/2009
(Continued)

OTHER PUBLICATIONS

Monte-Moreno, E., "Noninvasive estimate of blood glucose and blood pressure from a photoplethysmograph by means of machine learning techniques", Artificial Intelligence in Medicine, 2011, pp. 127-138 (12 pages total).
(Continued)

Primary Examiner — William J Levicky
Assistant Examiner — Naveed R. Kolia
(74) Attorney, Agent, or Firm — Sughrue Mion, PLLC

(57) ABSTRACT

An apparatus for health care which guides a user to measure a target component. According to one embodiment, the apparatus for health care may include a physiological information acquirer configured to acquire physiological information related to a target component and a processor configured to monitor a measurement event of the target component based on the acquired physiological information and guide a user to measure the target component based on a monitoring result.

25 Claims, 18 Drawing Sheets

(51) Int. Cl.

| | | |
|---|---|---|
| *A61B 5/02* | (2006.01) | |
| *A61B 5/021* | (2006.01) | |
| *A61B 5/024* | (2006.01) | |
| *A61B 5/026* | (2006.01) | |
| *A61B 5/08* | (2006.01) | |
| *A61B 5/145* | (2006.01) | |
| *A61B 5/16* | (2006.01) | |

(52) U.S. Cl.
CPC ....... *A61B 5/02035* (2013.01); *A61B 5/02405* (2013.01); *A61B 5/02416* (2013.01); *A61B 5/08* (2013.01); *A61B 5/14532* (2013.01); *A61B 5/14535* (2013.01); *A61B 5/14546* (2013.01); *A61B 5/165* (2013.01); *A61B 5/443* (2013.01); *A61B 2560/0431* (2013.01)

(56) References Cited

U.S. PATENT DOCUMENTS

| | | | | |
|---|---|---|---|---|
| 8,195,308 | B2* | 6/2012 | Frank | A61N 1/37512 |
| | | | | 607/122 |
| 10,555,677 | B2* | 2/2020 | Fleischer | A61B 5/7405 |
| 10,595,755 | B2* | 3/2020 | Zalevsky | G01B 9/02094 |
| 2010/0036221 | A1 | 2/2010 | Lee et al. | |
| 2014/0276556 | A1* | 9/2014 | Saint | G16H 40/63 |
| | | | | 604/504 |
| 2016/0157733 | A1 | 6/2016 | Gil | |

FOREIGN PATENT DOCUMENTS

| | | |
|---|---|---|
| JP | 2014-147637 A | 8/2014 |
| KR | 10-2010-0022614 A | 3/2010 |
| KR | 10-2011-0094405 A | 8/2011 |
| KR | 10-2012-0043189 A | 5/2012 |
| KR | 10-1512076 B1 | 4/2015 |
| KR | 10-2016-0075230 A | 6/2016 |
| KR | 10-2019-0065090 A | 6/2019 |
| WO | 2015167251 A1 | 11/2015 |
| WO | 2018/119663 A1 | 7/2018 |

OTHER PUBLICATIONS

Geng et al., "Noninvasive Continuous Glucose Monitoring Using a Multisensor-Based Glucometer and Time Series Analysis", Scientific Reports, Oct. 4, 2017, pp. 1-10 (10 pages total).

Man et al., "Meal Simulation Model of the Glucose-Insulin System", IEEE Transactions on Biomedical Engineering, vol. 54, No. 10, Oct. 2007, pp. 1740-1749 (10 pages total).

Communication dated Feb. 6, 2020 issued by the European Patent Office in counterpart European patent Application No. 19185145.0.

* cited by examiner

APPARATUS AND METHOD FOR HEALTH CARE

CROSS-REFERENCE TO RELATED APPLICATION(S)

This application is based on and claims priority under 35 USC § 119(a) to Korean Patent Application No. 10-2018-0108141, filed on Sep. 11, 2018, in the Korean Intellectual Property Office, the disclosure of which is incorporated herein by reference in its entirety.

BACKGROUND

1. Field

The following disclosure relates to an apparatus and method for health care, and more specifically, relates to guides the timing of measuring a target component using physiological change information related to the target component to be measured, such as blood glucose.

2. Description of Related Art

Diabetes mellitus is a chronic disease which is difficult to treat and causes various complications, and hence a blood sugar level needs to be checked regularly to prevent any complications. When insulin is administered, blood sugar should be checked in order to prevent hypoglycemia and control the insulin dosage. Generally, measuring blood sugar requires an invasive method such as drawing blood with a finger prick. The method of measuring blood sugar in an invasive manner has high reliability of measurement, but the use of injection may cause pain during blood sampling, inconvenience, and a risk of infection. Recently, a method of non-invasive measurement of blood sugar using a spectrometer, without directly collecting blood, has been studied.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to an aspect of an embodiment, there is provided an apparatus for health care including: a physiological information acquirer configured to acquire physiological information related to a target component of a user; and a processor configured to monitor a change in a value of the target component based on the physiological information and guide the user on a time to measure the target component, based on a result of monitoring the change in the value of the target component.

The physiological information may include at least one of heart rate, pulse rate, heart rate variability, pulse rate variability, blood flow, viscosity, hematocrit, respiration, skin temperature, and moisture.

The processor may extract a feature value based on the physiological information and monitor the change in the value of the target component based on a change in the extracted feature value relative to a feature value at a reference point in time.

The processor may extract one or more feature values from the physiological information based on a characteristic of the user.

The processor is further configured to obtain heart rate variability or pulse rate variability from the physiological information, and monitor the change in the value of the target component based on a change in a tachogram pattern of the heart rate variability or the pulse rate variability of the physiological information.

In response to the value of the target component being outside a predetermined normal range, the processor may be further configured to generate at least one of information for guiding the user to measure the target component through the target component measurement sensor and a control signal for controlling the target component measurement sensor.

The processor may be further configured to receive a result of measuring the target component from the target component measurement sensor and generate information for guiding the user's health care based on the result of measuring the target component.

The apparatus may further include an output interface configured to output at least one of a result of monitoring the change in the value of the target component and the information generated by the processor.

The apparatus may further include a communication interface configured to transmit a control signal generated by the processor to a target component measurement apparatus and receive a target component measurement result from the target component measurement apparatus.

The target component may include one or more of blood glucose, cholesterol, triglyceride, protein, and uric acid.

According to an aspect of another embodiment, there is provided a method for health care including: acquiring physiological information related to a target component of a user; monitoring change in a value of the target component based on the physiological information; and guiding the user on a time to measure the target component based on a result of monitoring the change in the value of the target component.

The monitoring may include extracting a feature value based on the physiological information and monitoring the target component based on a change in the extracted feature value relative to a feature value at a reference point in time.

The monitoring may include extracting one or more feature values from the physiological information based on a characteristic of the user.

The monitoring may include obtaining heart rate variability or pulse rate variability from the physiological information, and monitoring the change in the value of the target component based on a change in a tachogram pattern of the heart rate variability or the pulse rate variability of the physiological information.

The guiding the user on the time to measure the target component may include, in response to the value of the target component being outside a predetermined normal range, generating information for guiding the user to measure the target component through a target component measurement sensor and outputting the generated information to the user.

The guiding the user on the time to measure the target component may include, in response to the value of the target component being outside a predetermined normal range, generating a control signal for controlling a target component measurement apparatus and transmitting the generated control signal to the target component measurement apparatus.

The method may further include, when the target component is measured by a target component measurement apparatus, receiving a measurement result of the target component from the target component measurement apparatus; generating information for guiding health care of the user based on the measurement result received from the target component measurement apparatus; and outputting at least one of the measurement result received from the target component measurement apparatus and the information for guiding the health care of the user.

According to an aspect of another embodiment, there is provided an electronic device including: a pulse wave measurer configured to measure a pulse wave signal from a user; and a processor configured to acquire physiological information related to a first component of the user based on the pulse wave signal, monitor a change in a value of the first component based on the physiological information, and guide the user on a time to measure the first component based on a result of monitoring the change in the value of the first component.

The pulse wave measurer may include one or more light sources configured to emit light to the user and one or more detectors configured to detect light scattered or reflected from the user.

The processor may estimate, based on the pulse wave signal, a second component that includes one or more of blood pressure, vascular age, a degree of arteriosclerosis, aortic pressure waveform, vascular compliance, stress index, and a degree of fatigue.

The electronic device may further include a contact pressure measurer configured to a contact pressure between the user and the pulse wave measurer when the user is in contact with the pulse wave measurer, wherein the processor estimates the second component based on the pulse wave signal and the contact pressure.

The processor may estimate pulse rate variability based on the pulse wave signal and monitor the change in the value the first component based on the estimated pulse rate variability.

The processor may extract a feature value based on the pulse rate variability and monitor the first component based on a change in the extracted feature value relative to a feature value at a reference point in time.

The processor may acquire a tachogram of the pulse rate variability and monitor the change in the value of the first component based on a change in a pattern of the tachogram.

The electronic device may further include an output interface configured to, in response to the value of the first component being outside a predetermined normal range, output information for guiding the user on the time to measure the first component.

The electronic device may further include a communication interface configured to, in response to the value of the first component being outside a predetermined normal range, transmit a control signal for controlling the measurement of the first component to an external device.

The first component may include at least one of blood glucose, cholesterol, triglyceride, protein, and uric acid and the external device includes a device that measures the first component in a non-invasive.

The electronic device may further include a spectrum measurer configured to measure a spectrum for estimating the first component from the object of interest, wherein the processor may monitor the spectrum, and determine the value of the first component based on the physiological information and the spectrum.

The spectrum measurer may measure the spectrum using at least one of near-infrared spectroscopy, mid-infrared spectroscopy, and Raman spectroscopy.

BRIEF DESCRIPTION OF THE DRAWINGS

The above and/or other aspects will be more apparent by describing certain example embodiments, with reference to the accompanying drawings, in which.

Figure 1A:
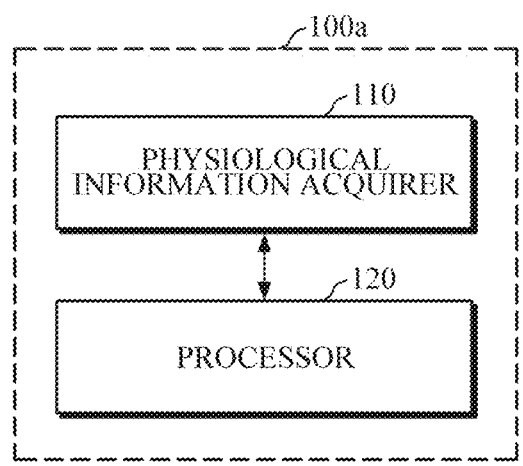
FIGS. 1A and 1B are block diagrams an apparatus for health care according to embodiments.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses and/or systems described herein. Various changes, modifications, and equivalents of the systems, apparatuses and/or methods described herein will suggest themselves to those of ordinary skill in the art. In the following description, a detailed description of known functions and configurations incorporated herein will be omitted when it may obscure the subject matter with unnecessary detail. Throughout the drawings and the detailed description, unless otherwise described, the same drawing reference numerals will be understood to refer to the same elements, features, and structures. The relative size and depiction of these elements may be exaggerated for clarity, illustration, and convenience.

It will be understood that, although the terms "first," "second," etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises" or "comprising" will be understood to imply the inclusion of stated elements but not the exclusion of any other elements. Terms such as "unit" and "module" denote units that process at least one function or operation, and they may be implemented by using hardware, software, or a combination of hardware and software.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Hereinafter, embodiments of an apparatus and method for health care will be described with reference to the accompanying drawings.

Figure 1B:
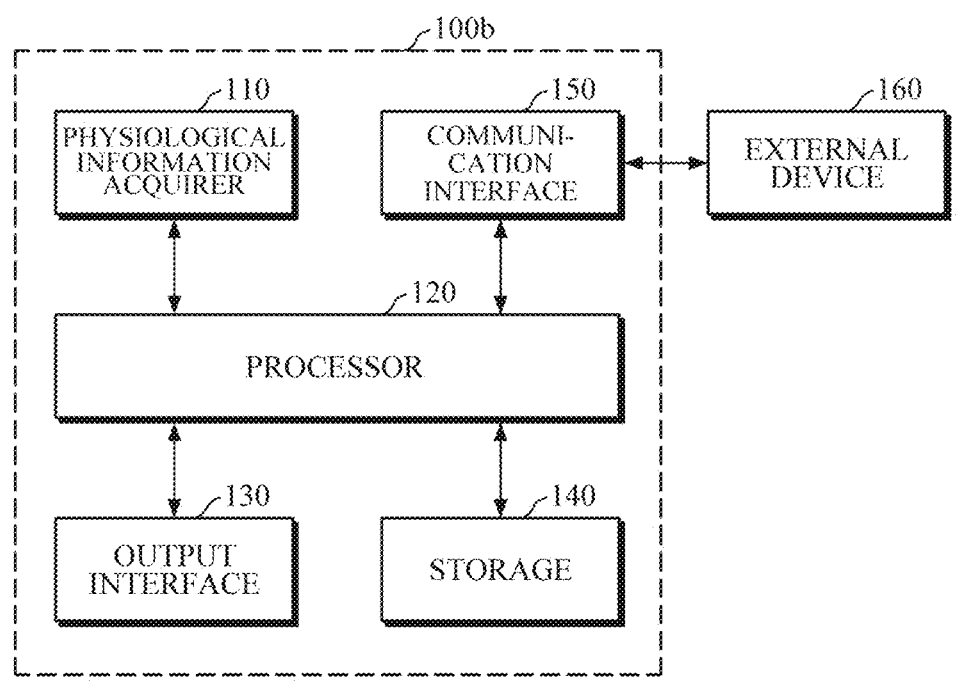

FIGS. 1A and 1B are block diagrams an apparatus for health care according to embodiments. FIGS. 2A to 2E are diagrams for describing measurement of physiological information related to a component of interest. FIGS. 3A to 3D are diagrams illustrating examples of blood glucose measurement guide. FIGS. 4A and 4B are examples of health care guide.

The apparatuses 100a and 100b for health care according to embodiments may be mounted in an electronic device, such as a smartphone, a tablet personal computer (PC), a desktop PC, a notebook PC, or the like, or a medical device of a specialized medical institution. Alternatively, the apparatuses 100a and 100b may be manufactured in an independent form, such as a wearable device of a wristwatch type, a bracelet type, a wrist band type, a ring type, a spectacle type, a hairband type, or the like, which can be worn on an object of interest.

Referring to FIG. 1A, the apparatus 100a for health care includes a physiological information acquirer 110 and a processor 120.

The physiological information acquirer 110 may acquire physiological information related to a target component to be monitored for health management. In particular, the target component includes at least one of blood glucose, cholesterol, triglyceride, protein, and uric acid, but is not limited thereto. For convenience of explanation, blood glucose will be described as an example of the target component.

Figure 2A:
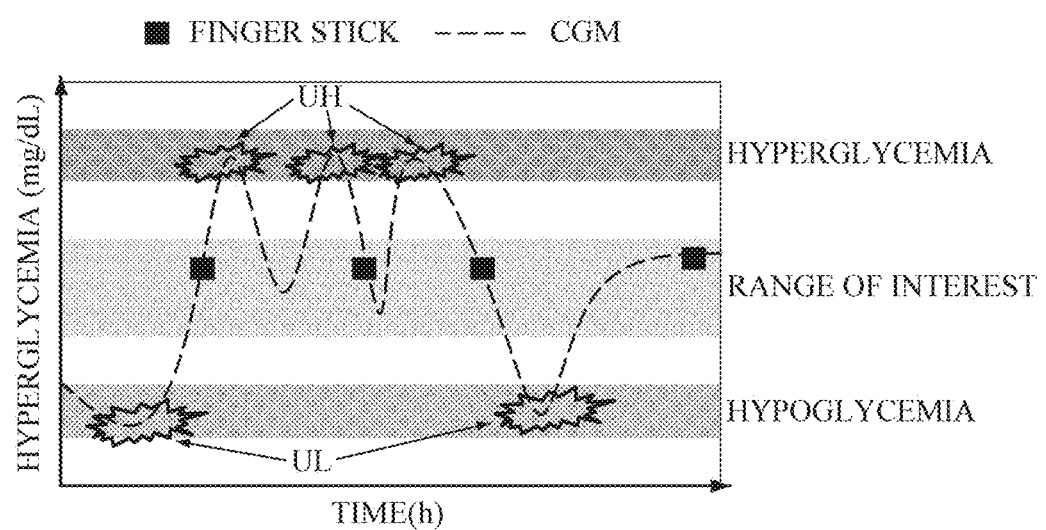
FIGS. 2A, 2B, 2C, 2D, and 2E are diagrams for describing measurement of physiological information related to a target component.

FIG. 2A shows blood glucose variability throughout a day. As shown in FIG. 2A, hypoglycemia, normal blood glucose and hyperglycemia occur due to various causes during the day. For the purpose of blood glucose control, oral glucose tolerance test, measurement of 2-hour postprandial blood glucose, and measurement of fasting blood glucose may periodically performed through finger sampling (e.g., capillary sampling from a finger using a finger stick). Alternatively, blood glucose variability may be monitored by continuously measuring blood glucose through a non-invasive continuous glucose monitoring (CGM) device. However, when blood glucose is periodically measured by finger sampling or the like, hypoglycemia (UL) or hyperglycemia (UH) may not be detected if hypoglycemia (UL) or hyperglycemia (UH) occurs during the interval between the periodic measurements. On the other hand, when blood glucose is continuously measured by a non-invasive CGM device, computational load may increase and memory resources may be exhausted.

The physiological information acquirer 110 may acquire physiological information that is affected by a change in the target component, for example, heart rate, pulse rate, heart rate variability (HRV), pulse rate variability (PRV), blood flow, viscosity, hematocrit, respiration, skin temperature, moisture, and the like. However, examples of the physiological information are not particularly limited.

The physiological information acquirer 110 may include one or more sensors for measuring a photoplethysmogram (PPG) signal, an electrocardiography (ECG) signal, an electromyography (EMG) signal, a ballistocardiogram (BCG) signal, skin temperature, moisture, pulse pressure, and the like, and acquire physiological information related to a target component by analyzing a sensor signal. The one or more sensors may include an optical sensor, a PPG sensor, an ECG sensor, an EMG sensor, a BCG sensor, a temperature sensor, a moisture sensor, and a pulse pressure sensor. For example, the physiological information acquirer 110 may estimate pulse rate variability or heart rate variability by analyzing a PPG signal or an ECG. The physiological information acquirer 110 may continuously acquire physiological information through a sensor for a predetermined period of time. In another embodiment of the present disclosure, the estimation of pulse rate variability or heart rate variability and the analysis of the PPG signal and the ECG may be performed by the processor 120. However, the various embodiments of the present disclosure are not limited to the above description, and it is possible to acquire physiological information from input by a user or from an external device. In such a case, the physiological information acquirer 110 may be realized as an input interface, or a communication module/interface.

Figure 2B:
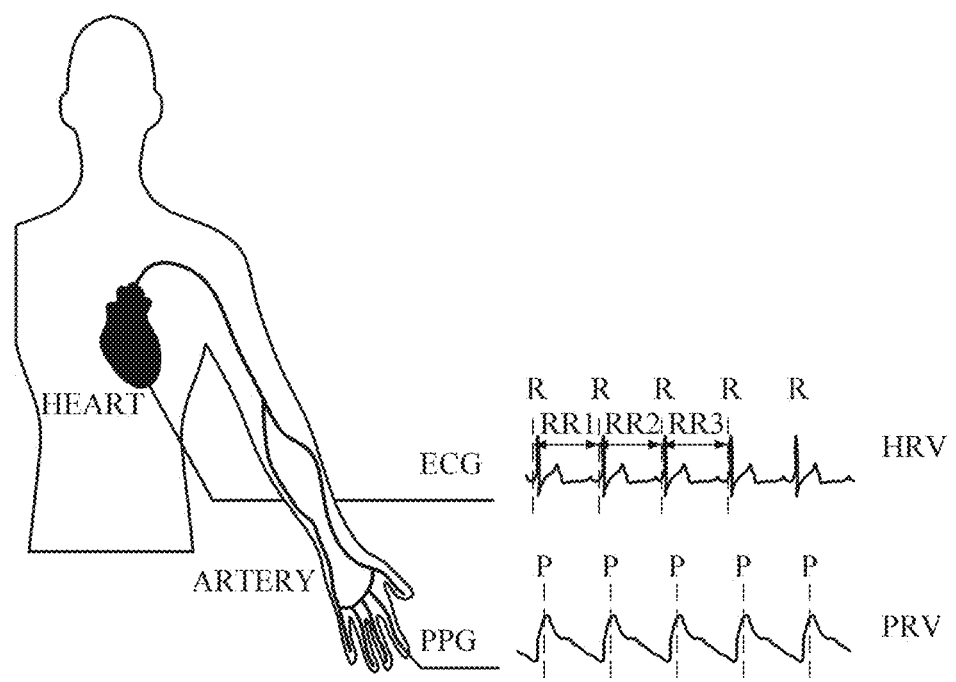
Figure 2C:
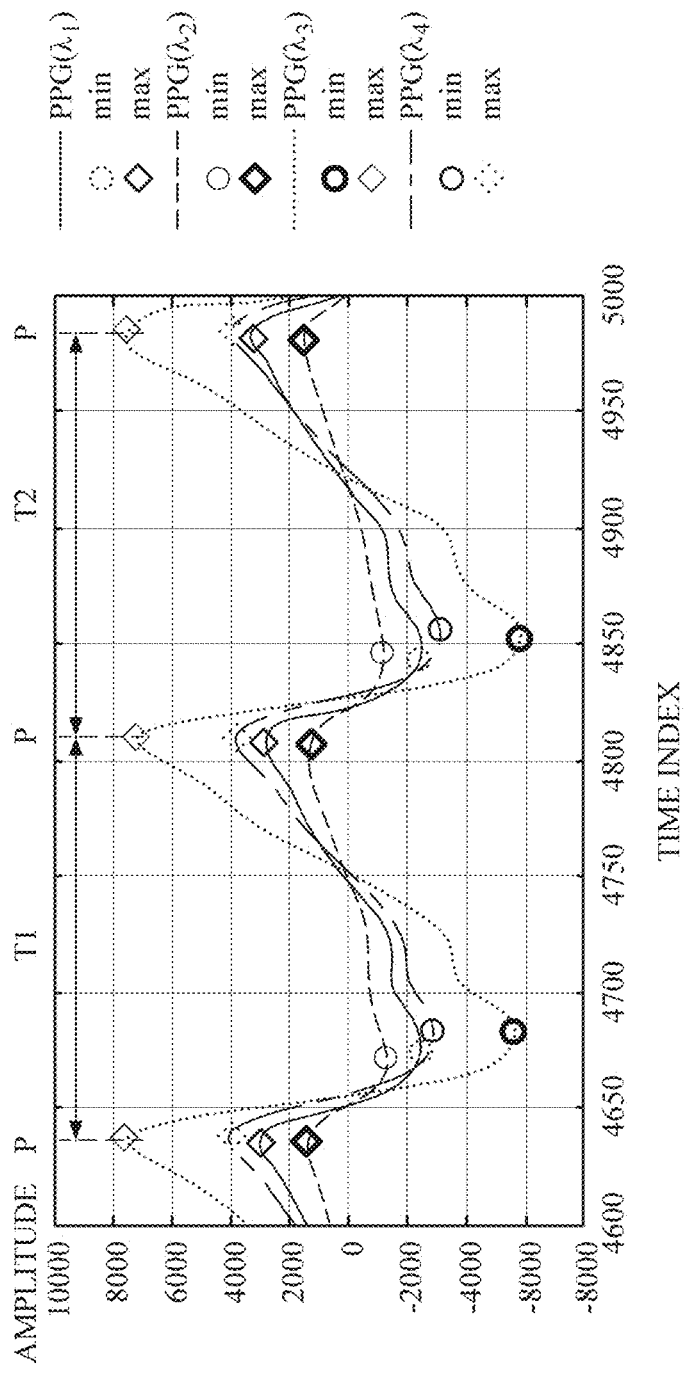

Referring to FIGS. 2B and 2C, the physiological information acquirer 110 may measure an ECG signal and/or pulse wave signals (PPG signal) of multiple wavelengths from the user and estimate HRV or PRV based on peak-to-peak intervals of an HRV signal and peak-to-peak intervals of an PRV signal. As shown in FIG. 2B, the peaks of the HRV signal and the PRV signal are denoted as R and P, respectively. The peak-to-peak intervals of the HRV signal and the PRV signal may be also referred to as RR intervals and PP intervals. The RR intervals may include interval RR1, interval RR2, and interval RR3 of the ECG signal. For example, as shown in FIG. 2C, the physiological information acquirer 110 may acquire pulse wave signals of multiple wavelengths $\lambda_1$, $\lambda_2$, $\lambda_3$, and $\lambda_4$ and estimate PRV by analyzing the PP intervals T1 and T2 of the acquired pulse wave signals of multiple wavelengths.

The processor 120 may monitor a measurement event of a target component using the acquired physiological information and guide the user to measure the target component when a measurement event of the target component occurs. For example, when the user exhibits symptoms, such as sweating, nervousness, shakiness, loss of consciousness, palpitation, hunger, dizziness, fatigue, weakness, headache, and confusion, hypoglycemia may be suspected. At this time, a physiological change indicating a hypoglycemic symptom occurs in the human body, and the processor 120 may determine a hypoglycemic state in which blood glucose measurement is required by analyzing the physiological information obtained at this point, such as skin temperature, moisture, respiration, heart beat variability, and pulse variability.

The processor 120 may extract a feature by analyzing the physiological information and monitor the measurement event of a target component based on a change in the extracted feature value relative to a feature value at a reference point in time. The processor 120 may monitor the change in the extracted feature value during a time period between the extraction time of the feature value and the reference point in time.

For example, the processor 120 may extract various time domain feature values through time-series pattern analysis of HRV or PRV in time domain. For example, the time domain feature values may include mean HRT, standard deviation of NN intervals (SDNN), a root mean square of successive differences between adjacent NN intervals (RMSSD), a ratio of the number of pairs of adjacent RR intervals differing by more than 20 ms to a total number of the RR intervals (pNN20), a ratio of the number of pairs of adjacent RR intervals differing by more than 50 ms to the total number of the RR intervals (pNN50), and the like. However, the feature values are not limited to the above examples.

In another embodiment, the processor 120 may transform HRV or PRV in time domain into frequency domain through Fourier transform or the like, and extract various frequency domain feature values through a spectrum analysis of a different wavelength. For example, the frequency domain feature values may include power in very low frequency range (VLF), power in low frequency range (LF), power in high frequency range (HF), an LF/HF ratio, and the like. However, the feature values are not limited to the above examples.

The processor 120 may compare the extracted feature value with a feature value at the reference point in time, and when a change of the extracted feature value relative to the feature value at the reference point in time exceeds a preset threshold, the processor 120 may determine that a blood glucose measurement event, which indicates hypoglycemia/hyperglycemia/glucose metabolic abnormality, has occurred. Alternatively, when the extracted feature value exceeds a preset threshold, it may be determined that the blood glucose measurement event has occurred. At this time, the reference point in time may be an arbitrary point in time at which blood glucose is normal or be a point in a fasting state. The preset threshold may the highest value and/or the lowest value of a normal range and may be set according to the type of a target component.

In one example, in the case of hyperglycemia, in order to maintain homeostasis in the human body, a parasympathetic nerve is activated in an attempt to reduce blood glucose. For example, HF of the frequency domain feature, and RMSSD and pNN50 of the time domain features are increased in a hyperglycemia state, as compared to those measured in a normal blood glucose state. As such, when a feature value, such as RMSSD or pNN50, exceeds the threshold, it may be determined that a hyperglycemia event has occurred.

In another example, in the case of hypoglycemia, in order to maintain homeostasis, a sympathetic nerve is activated in an attempt to increase blood glucose. For example, LF of the frequency domain feature and SDNN of the time domain feature are increased in a hypoglycemia state, as compared to those measured in the normal blood glucose. As such, when LF or SDNN exceeds the preset threshold, it may be determined that a hypoglycemia event has occurred.

In still another example, when an LF/HF ratio abruptly changes as compared to the reference point in time, the processor 120 may determine that glucose metabolic abnormality has occurred. For example, when the change in the LF/HF ratio during a predetermined time period is greater than a threshold value, the processor 120 may determine that glucose metabolic abnormality has occurred.

Meanwhile, even when the target components to be analyzed are the same, the processor 120 may monitor the target component measurement event using different types of physiological information and/or feature values according to user characteristics, such as a health state.

For example, when a user has a greater change in skin moisture than other types of physiological information according to the blood glucose change, the blood glucose measurement event for the user may be monitored using skin moisture acquired from the user. In another example, two or more types of physiological information of each user that reflects well a change of a target component are applied a weight and combined, and a combined result is compared with a corresponding value at the reference point in time. In this case, the weight may be predefined based on a degree to which each piece of physiological information reflects a change of a target component. In still another example, one or two or more pieces of physiological information that reflects well a change of blood glucose of the user among various extractable feature values may be combined and used in monitoring the user's blood glucose measurement event. In this case, when two or more feature values are used, a weight may be applied to each of the feature values and then weighted feature values may be combined.

Figure 2D:
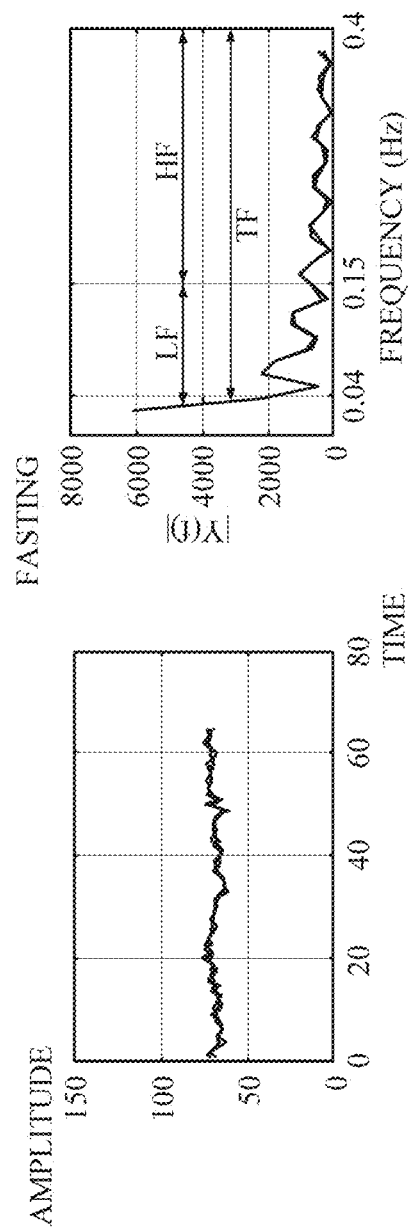
Figure 2E:
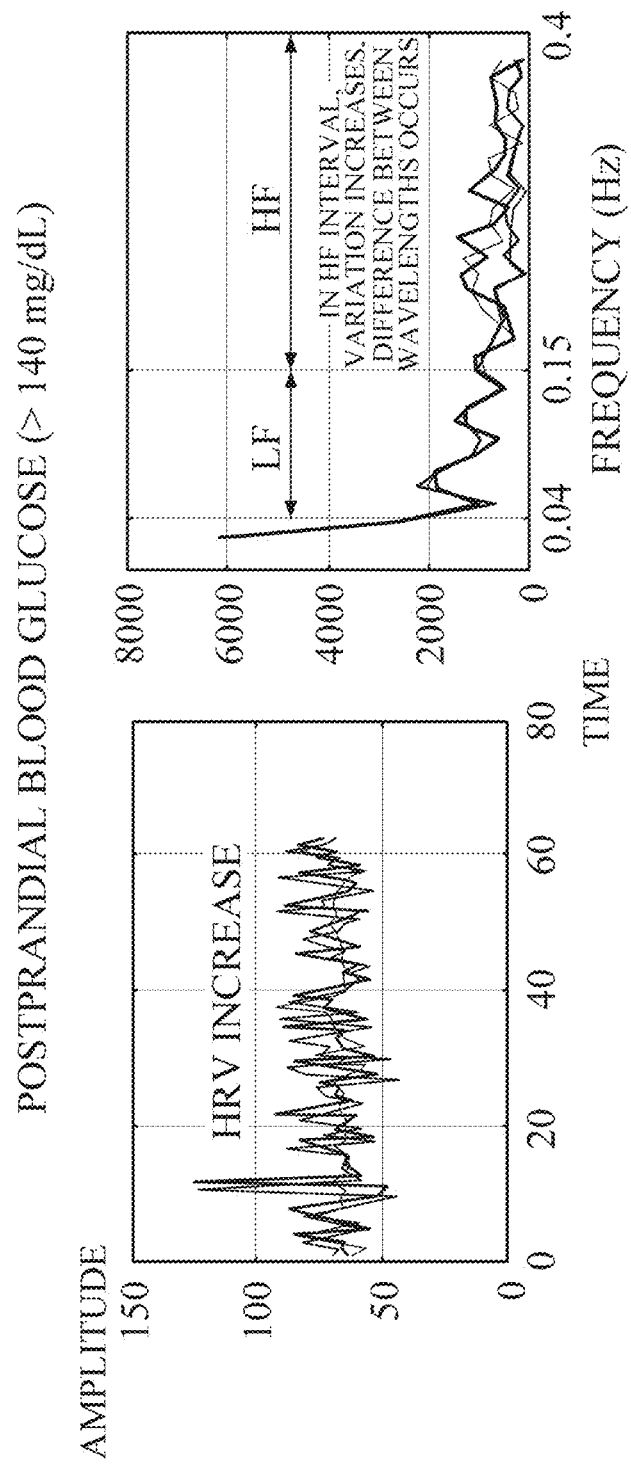

Referring to FIGS. 2D and 2E, the processor 120 may monitor a measurement event of a target component based on a tachogram pattern change in PRV or HRV. FIG. 2D is a tachogram of PRV at a reference point in time, for example, in a fasting state. FIG. 2E is a tachogram when postprandial blood glucose level is higher than 140 mg/dL. As shown in FIGS. 2D and 2E, it can be seen that in a postprandial hyperglycemic state, HRV is increased, and accordingly, variation is increased in an HF interval, which is a frequency domain feature, and a difference between wavelengths occurs.

When the measurement event of a target component occurs, the processor 120 may guide the user to measure the target component through an apparatus for measuring a target component. The apparatus for measuring a target component may be mounted in the apparatus 100a or may be a separate external device. The processor 120 may provide a guide for an action to be taken by the user, timing and method for measuring the target component, or the like.

For example, when it is determined, as a result of monitoring, that hypoglycemia/hyperglycemia/glucose metabolic abnormality has occurred, the processor 120 may guide the user to measure blood glucose using a blood glucose measurement apparatus. The blood glucose measurement apparatus may be an apparatus capable of continuously or discontinuously measuring blood glucose based on an invasive, minimally invasive, or non-invasive method, and may not be particularly limited to a certain type. In addition, the processor 120 may generate a control signal for controlling blood glucose measurement of the blood glucose measurement apparatus and transmit the control signal to the blood glucose measurement apparatus.

Referring to FIG. 1B, the apparatus 100b for health care according to another embodiment may further include an output interface 130, a storage 140, and a communication interface 150 in addition to the elements of the apparatus 100a for health care shown in FIG. 1A.

The output interface 130 may output a processing result of the processor 120 to the user. For example, when a target component measurement event occurs, the processor 130 may generate guide information related to the target component, and the output interface 130 may output the guide information generated by the processor 130.

Figure 3A:
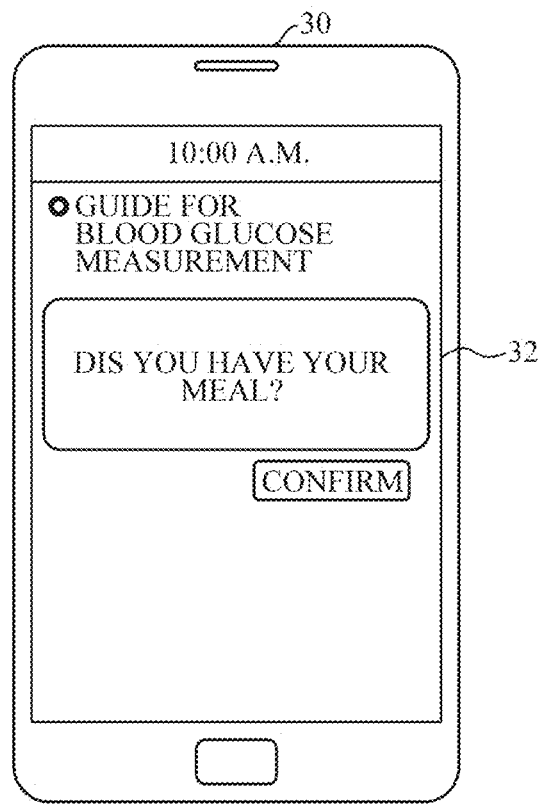
FIGS. 3A, 3B, 3C, and 3D are diagrams illustrating examples of blood glucose measurement guide.
Figure 4A:
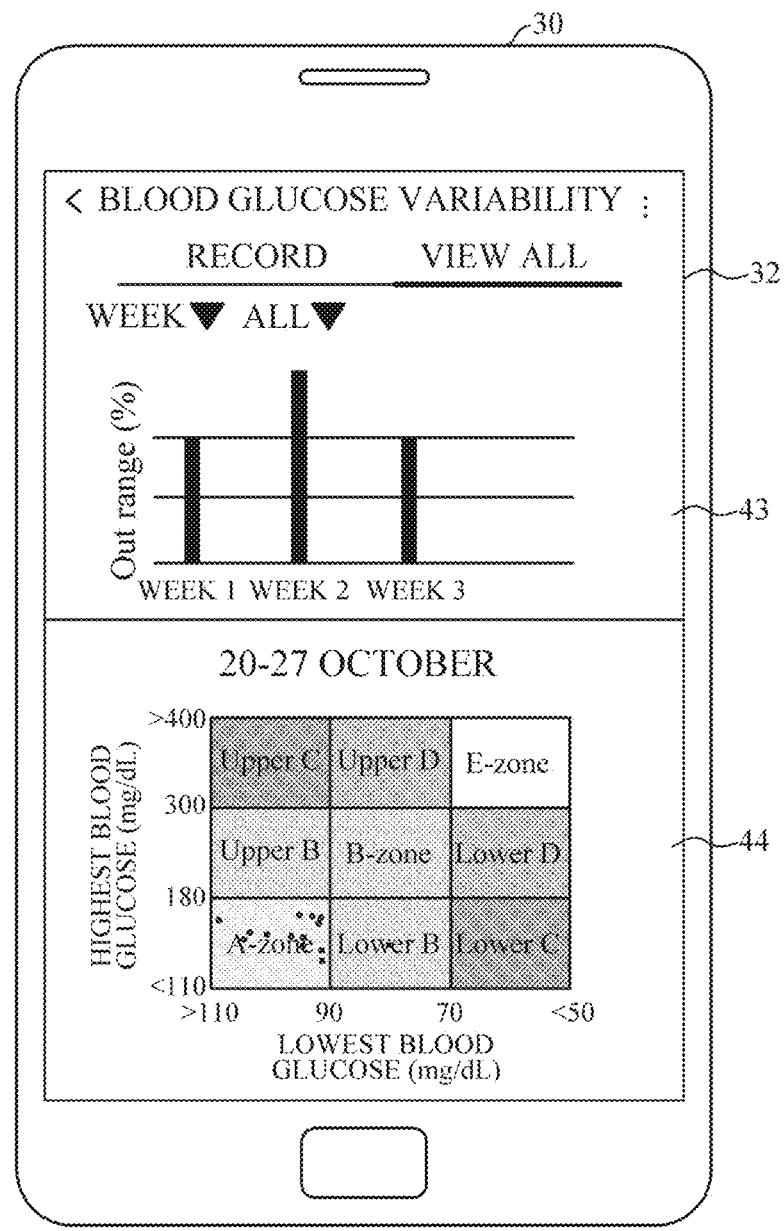
FIGS. 4A and 4B are examples of health care guide.
Figure 4B:
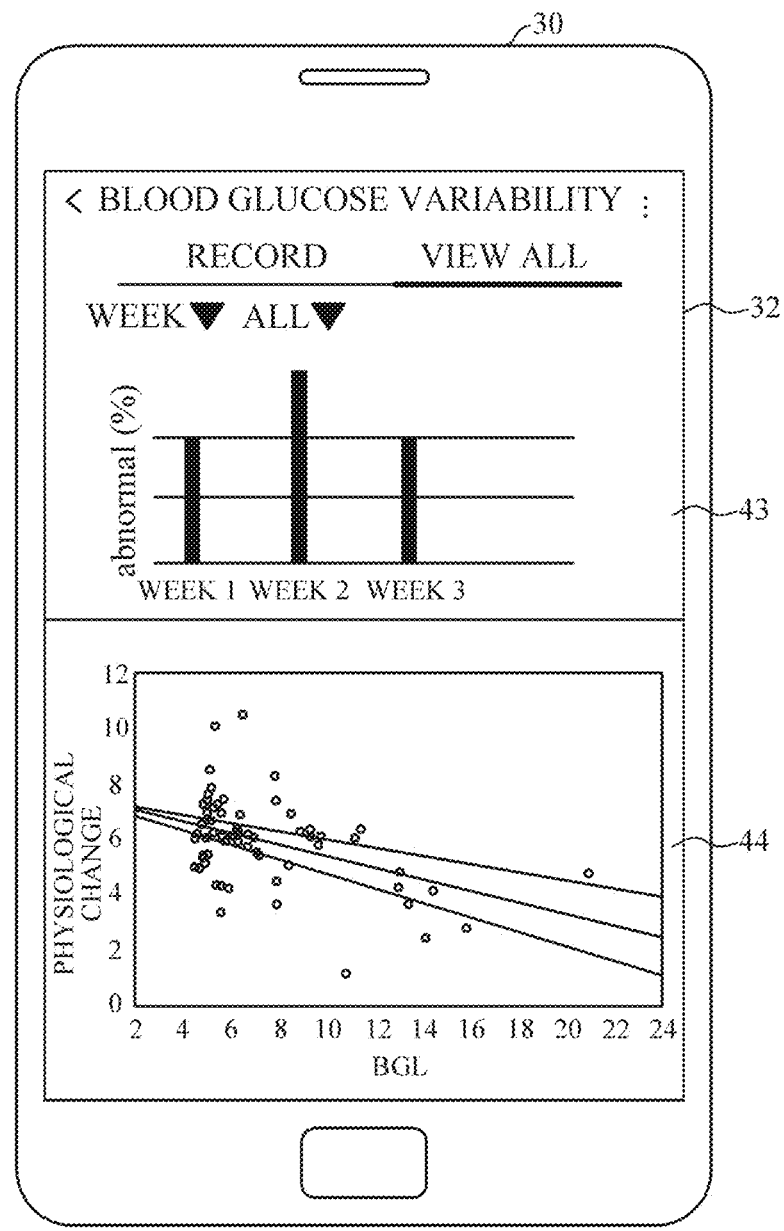

In one example, referring to FIG. 3A, the apparatus 100b for health care may be mounted in a smartphone 30. However, as described above, it is apparent that various embodiments of the apparatus for health care are not limited to being mounted only in the smartphone 30.

When a blood glucose event occurs, the processor 120 may provide the user with guide information about an action to be taken according to the blood glucose event. For example, when a hypoglycemic state is predicted, the processor 120 may generate guide information, such as "Did you have a meal?" The guide information is not limited to the above example, and may be generated as, for example, "Please check your existing health care," "Please have a small amount of meal several times, rather than a large amount at a time," or the like, according to various situations where a blood glucose event, such as hyperglycemia, hypoglycemia, or glucose metabolic abnormality, occurs.

The output interface 130 may include a display 32, a speaker, and/or a haptic motor. The output interface 130 may visually output the generated guide information through the display 32 of the smartphone 30. However, the embodiment is not limited to the above example, and the generated guide information may be output through, for example, a speaker of the smartphone 30. In addition, the occurrence of blood glucose event may be informed to the user through vibration of the haptic motor of the smartphone 30.

Figure 3B:
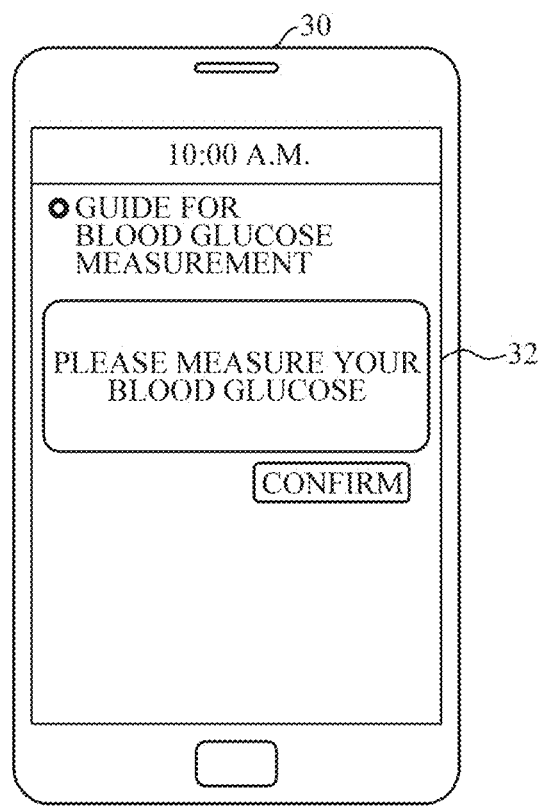

In another example, referring to FIG. 3B, when the processor 120 determines that a blood glucose event has occurred, the processor 120 may generate guide information, such as "Please measure your blood glucose level immediately," to encourage the user to measure blood glucose promptly, and the output interface 130 may output the generated guide information to the display 32 of the smartphone 30. However, the embodiment is not limited to the above example, and the processor 120 may provide guide information, such as "Please measure your blood glucose level within an hour," to encourage the user to measure blood glucose within a predetermined time according to a current blood glucose state. The user may measure a target component by driving a target component measurement sensor according to the guide.

The communication interface 150 may communicate with an external device 160 under the control of the processor 120. In this case, the external device 160 may include, but is not limited to, an invasive or minimally invasive blood glucose measurement device or devices such as a smartphone, a tablet PC, a desktop PC, a notebook PC, and a wearable device, which are equipped with a function of non-invasively measuring blood glucose.

The communication interface 150 may access a communication network using a communication technology, such as Bluetooth communication, Bluetooth low energy (BLE) communication, near field communication (NFC), wireless local access network (WLAN) communication, ZigBee communication, infrared data association (IrDA) communication, Wi-Fi direct (WFD) communication, ultra-wideband (UWB) communication, Ant+ communication, Wi-Fi communication, radio frequency identification (RFID) communication, 3G communication, 4G communication, and 5G communication. However, the communication technology is not limited to the above examples.

The processor 120 may control the communication interface 150 to be connected with the external device 160 when the occurrence of a measurement event of a target component is detected as a result of monitoring. In addition, the processor 120 may generate a control signal for controlling the external device 160 and transmit the control signal to the external device 160 through the communication interface 150. Also, when the target component is measured through the external device 160, the processor 120 may receive a measurement result of the target component from the external device 160 through the communication interface 150.

Figure 3C:
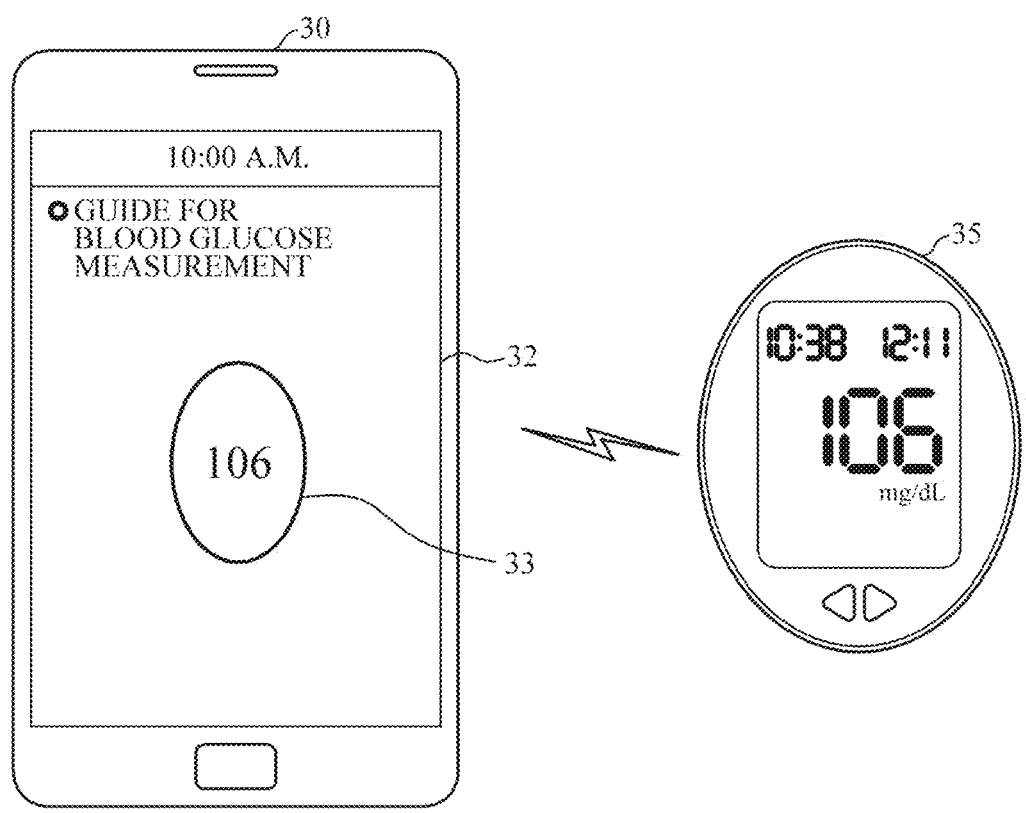

In one example, referring to FIG. 3C, the processor 130 may be connected to a blood glucose measurement device 35 through the communication interface 150 and, when the blood glucose measurement device 35 measures blood glucose, the processor 130 may output visual information indicating the connection to the blood glucose measurement device 35 to the display 32. In particular, the visual information may include a visual object, such as an image representing the blood glucose measurement device, and/or the blood glucose measurement result.

Figure 3D:
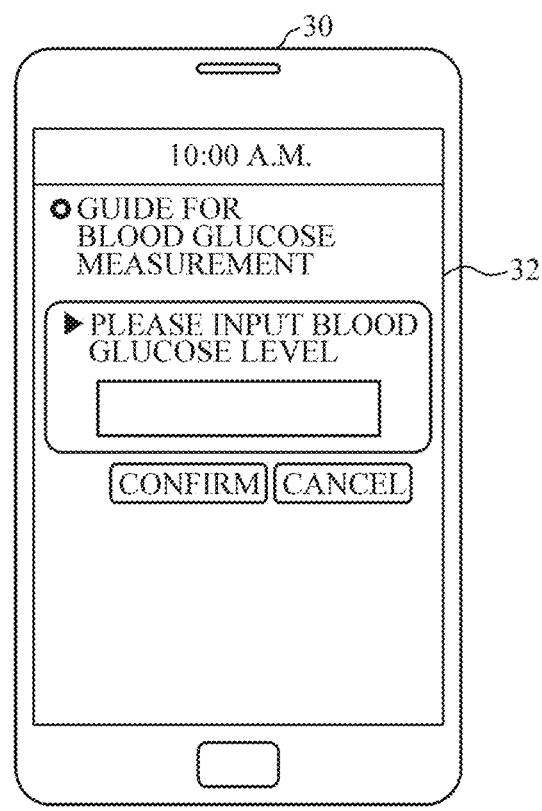

In another example, referring to FIG. 3D, after providing a guide related to an occurrence of the blood glucose measurement event to the user, or in response to a user's request, the processor 120 may output an interface for inputting a blood glucose measurement result to the display 32 of the smartphone 30 through the output interface 130. Once the blood glucose measurement is completed, the user may input the blood glucose measurement result through the interface.

The physiological information acquired by the physiological information acquirer 110, a processing result of the processor 120, and the target component measurement result acquired from the communication interface 150 or from the input of the user may be stored in the storage 140. In addition, user characteristic information, such as user's health status, age, sex, and the like or reference information, such as a type of a feature value to be used for each user, a threshold, and the like, which is used for monitoring a target component measurement event may be stored in the storage 140.

The storage 140 may include, but is not limited to, at least one type of storage medium, such as a flash memory type, a hard disk type, a multimedia card micro type, a card type memory (e.g., SD or XD memory) random access memory (RAM), static random access memory (SRAM), read-only memory (ROM), electrically erasable programmable read-only memory (EEPROM), programmable read-only memory (PROM), a magnetic memory, a magnetic disk, and an optical disk.

In addition, when the processor 120 receives the target component measurement result, the processor 120 may generate a variety of information related to health based on the received measurement result and output the information through the output interface 130. For example, when the blood glucose measurement result is less than a preset threshold (e.g., 70 mg/dL), hypoglycemia is diagnosed, and as described with reference to FIG. 3A, health information, such as an action to be taken when the blood glucose event occurs or a change of dose of drug taken by the user may be provided.

Further, the processor 120 may track the results of the measurement of the target component for a predetermined period of time stored in the storage 140 to generate various health indices and provide the health indices to the user through the output interface 130. In one example, the processor 120 may generate a blood glucose score or a stress score indicative of a blood glucose metabolism state. For example, hypoglycemia/hyperglycemia frequency and/or stress frequency may be calculated by dividing the number of occurrences of hypoglycemia/hyperglycemia and/or the number of stresses for a predetermined period by the total number of data. Further, hypoglycemia/hyperglycemia period and/or stress period may be calculated by dividing hypoglycemia/hyperglycemia time and/or stress time by the total data time. In another example, together with or separately from the aforementioned indices, analytical information regarding the highest and lowest blood glucose levels per day for a predetermined period of time and/or information on changes in blood glucose and physiological response may be generated. These are merely examples, and various other health indices may be generated.

The output interface 130 may output the health indices generated by the processor 120 as shown in FIGS. 4A and 4B. FIG. 4A illustrates an example in which a blood glucose score and/or a stress score are output to a first region 43 of the display 32 and analytical information regarding the highest and lowest blood glucose levels per day for a predetermined period of time is output to a second region 44. FIG. 4B illustrates an example in which the blood glucose score or the stress score is output to the first region 43 of the display 32 and information on changes in blood glucose and physiological response is output to the second region 44. The first region 43 may show a ratio of an abnormal time period during which the user's blood glucose level was outside a normal/reference glucose range (e.g. 20 hours, 30 hours, etc.), to the entire monitoring time period (e.g., week 1, week 2, etc.). The second region 44 may show a change in a physiological feature value according to a change in a blood glucose level (BGL), along with measurement times (e.g., Day 1, Day 5, Day 10, and Day 30). However, these are merely examples, and any piece of information may be output to the entire area of the display 32. Also, when the user selects one of two pieces of information output to each region 43 and 44, the selected information may be enlarged and output across the entire area of the display 32.

According to the disclosed embodiments, timing for measuring a target component through physiological information that affects a change of the target component can be informed, without the need to continuously measure the target component, such as blood glucose, and hence it is possible to prevent degradation of computing performance due to continuous measurement of the target component and to efficiently manage memory space.

Figure 5:
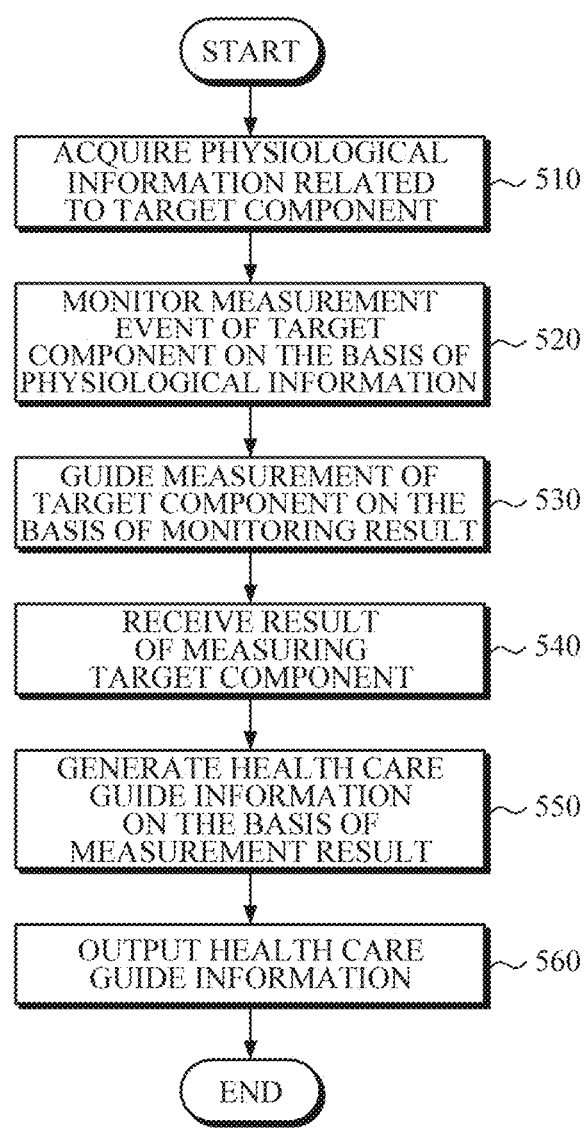
FIG. 5 is a flowchart illustrating a method for health care according to one embodiment.

FIG. 5 is a flowchart illustrating a method for health care according to an embodiment. The embodiment shown in FIG. 5 may be performed by the apparatuses 100a and 100b for health care in accordance with the embodiments of FIGS. 1 and 2. Hereinafter, the method will be briefly described.

First, physiological information related to a target component may be acquired in operation 510. The physiological information, such as heart rate, pulse rate, HRV, PRV, blood flow, viscosity, hematocrit, respiration, skin temperature, moisture, and the like, may be acquired through one or more sensors capable for measuring a PPG signal, an ECG signal, an EMG signal, a BCG signal, pulse pressure, moisture, skin temperature, and the like.

Then, a measurement event of the target component may be monitored based on the acquired physiological information in operation 520. For example, time domain and/or frequency domain feature values may be extracted based on PRV of a PPG signal or HRV of an ECG signal, and when the extracted feature value is outside a preset threshold range or when a change in a feature value relative to a reference point in time is outside another preset threshold range, it may be determined that a blood glucose event which requires blood glucose measurement has occurred. Alternatively, whether the blood glucose event has occurred may be determined based on a change in tachogram pattern of PRV or HRV relative to a reference point in time.

Then, the measurement of the target component may be guided based on the monitoring result in operation 530. For example, information on an action to be taken by the user depending on a state of a target component, a medicine guide, and the timing and method for measuring a target component may be provided to the user.

Then, when the user measures the target component using a target component measurement sensor, a measurement result of the target component may be received in operation 540. The target component measurement sensor may be a blood glucose meter using a lancet and a glucose test strip. For example, when the apparatus 100a/100b for health care communicates with a target component measurement device, the apparatus 100a/100b may directly receive the measurement result from the target component measurement device, and otherwise, the apparatus may 100a/100b receive the measurement result input by the user.

Then, health care guide information, health indices, and the like may be generated based on the measurement result of the target component in operation 550. In particular, the health care guide information may include an action to be taken by the user depending on normal state, hypoglycemia, hyperglycemia, or the like, health knowledge, and the like. Also, the health indices may include a blood glucose score, a stress score, the highest and lowest blood glucose levels for a predetermined period of time, information on changes in blood glucose and physiological response, and the like.

Then, the generated health care guide information may be output in operation 560. The user may be provided with the information through various methods using a display, a speaker, a haptic module, and the like.

Figure 6A:
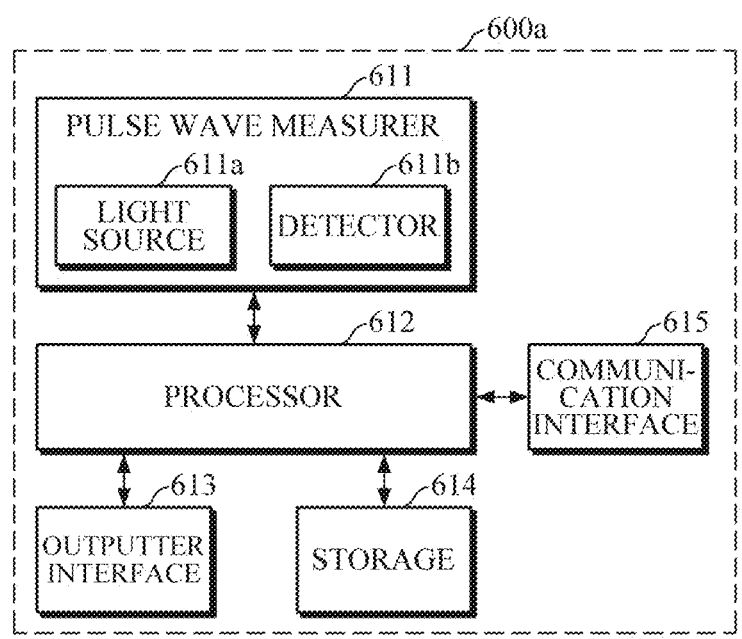
FIG. 6A is a block diagram illustrating an electronic device according to one embodiment.
Figure 6B:
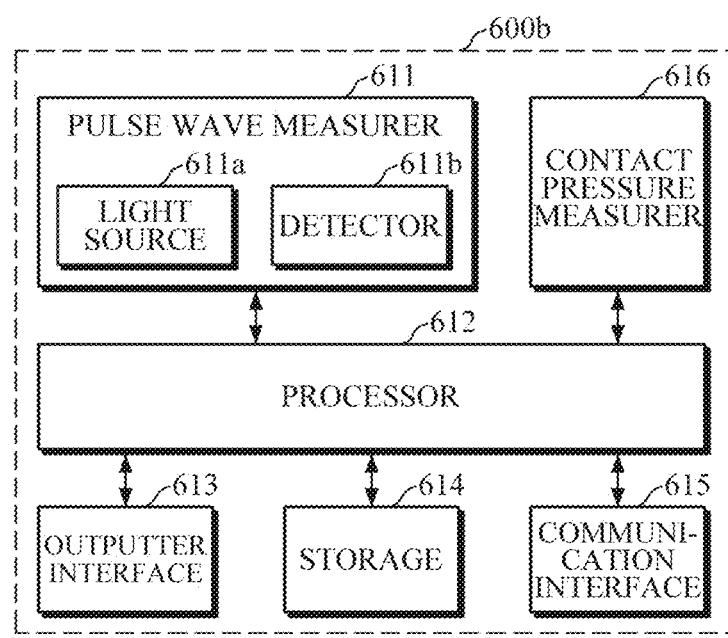
FIG. 6B is a block diagram illustrating an electronic device according to another embodiment.

FIGS. 6A and 6B are block diagrams illustrating electronic devices according to embodiments. The electronic devices 600a and 600b according to embodiments may be portable terminals, such as smartphone, tablet PCs, notebook PCs, wearable devices, and the like, but are not limited thereto. According to the present embodiments, the electronic devices 600a and 600b may estimate one component and at the same time guide a user to measure other components. For example, the electronic devices 600a and 600b may be continuous blood glucose measurement apparatuses and may guide the user to measure blood glucose, while estimating blood pressure.

Referring to FIG. 6A, the electronic device 600a includes a pulse wave measurer 611, a processor 612, an output interface 613, a storage 614, and a communication interface 615. Referring to FIG. 6B, the electronic device 600b may further include a contact pressure measurer 616.

The pulse wave measurer 611 may measure a pulse wave signal including a PPG signal. The pulse wave measure 611 may include a light source 611a and a detector 611b. The light source 611a may be formed of a light emitting diode (LED), a laser diode (LD), or a phosphor, but is not limited thereto. The light source 611a may be formed as one or two or more arrays, and each light source 611a may emit light of a different wavelength. The detector 611b may be formed of one or more pixels and each pixel may include a photodiode, a photo transistor (PTr), or an image sensor (e.g., complementary metal-oxide-semiconductor (CMOS) image sensor) which receives light scattered or reflected from an object of interest irradiated by the light source 611a. However, the detector 611b is not limited to the above examples. In addition, light sources 611a may be disposed at different distances from the detector 611b.

The processor 612 may acquire physiological information related to a first component based on the measured pulse wave signal. In particular, the first component may include at least one of blood glucose, cholesterol, triglyceride, protein, and uric acid. When the pulse wave signal is measured, the processor 612 may estimate PRV through analysis of RR periods of the pulse wave signal.

When the PRV is estimated, the processor 612 may extract features by analyzing the PRV in time domain and/or frequency domain, and guide the user to measure the first component based on the extracted feature values. The time domain features and the frequency domain features are as described above. For example, the occurrence of a blood glucose measurement event may be monitored by comparing the extracted feature value or a value of a change in the extracted feature value relative to a reference point in time with a preset threshold. In addition, the processor 612 may monitor the occurrence of a blood glucose measurement event based on a change in a tachogram pattern of the estimated PRV relative to a tachogram pattern of PRV at a reference point in time.

Moreover, the processor 612 may measure a second component based on the measured pulse wave signal. The second component may include blood pressure, vascular age, a degree of arteriosclerosis, aortic pressure waveform, vascular compliance, stress index, and a degree of fatigue, but is not limited thereto. The monitoring of the first component measurement event and the estimation of the second component may be performed at the same point in time according to the settings, and the monitoring of the first component measurement event may be performed only at a certain point in time, rather than each time the second component is estimated.

For example, the processor 612 may estimate blood pressure based on an oscillometric method using the pulse wave signal and a contact pressure. While the pulse wave signal is being measured, the user may be in contact with the pulse wave measurer 611 with an object of interest (e.g., a finger) and press the object of interest against the pulse wave measurer 611 to steadily increase a contact pressure on the pulse wave measurer 611, or the user may first strongly press the object of interest against the pulse wave measurer 611 and then gradually decrease a contact pressure on the pulse wave measurer 611. When the user whose finger is in contact with the pulse wave measurer 611 presses the finger against the pulse wave measurer 611 to gradually increase the contact pressure, a contact area and a contact time of the finger are increased, and the amount of light detected by each pixel of the detector 611b is also increased according to the increase of contact area and contact time.

The processor 612 may estimate the contact pressure based on a correlation between the amount of light received by each pixel and a contact pressure. Alternatively, referring to FIG. 6B, the contact pressure measurer 616 may measure a contact pressure between the object of interest and the pulse wave measurer 611 while the user is measuring a pulse wave signal by bringing the object of interest in contact with the pulse wave measurer 611. In this case, the contact pressure measurer 616 may include a force sensor and/or an area sensor. The processor 612 may estimate blood pressure based on an oscillometric method using the pulse wave signal and the contact pressure acquired as described above. However, the embodiment is not limited to the above description, and various other known blood pressure estimation techniques may be used to estimate blood pressure.

The output interface 613 may output the estimation result of the second component and guide information generated by the processor 612 regarding the measurement of the first component through various output means. For example, as described above, the guide information may include a guide related to an action of the user according to a blood glucose state, a guide related to the timing and/or method for measuring blood glucose, and a guide, if necessary, related to communication connection.

Various items of reference information required for monitoring the first component measurement event and/or estimating the second component, and/or the pulse wave signal measured by the pulse wave measurer 611, a processing result of the processor 612, and the like may be stored in the storage 614. For example, the reference information may include a threshold used for determining whether an event has occurred in connection with monitoring the first component measurement event, a type and a calculation method of a feature to be used for monitoring, and a measurement event determination period for the first component in the case of an apparatus for continuously measuring the second component. In addition, the reference information may include an estimation model and the estimation timing for estimating the second component. Further, the storage 614 may store user characteristic information, such as a health status of the user.

The communication interface 615 may communicate with an external device under the control of the processor 612. In this case, the external device may include a device for measuring the first component, and is not limited to a smartphone, a tablet PC, a desktop PC, a notebook PC, a wearable device, or the like. In this case, the device for measuring the first component may be a device capable of continuously or discontinuously measuring the first component based on an invasive, minimally invasive, or non-invasive method. The communication interface 615 may transmit a control signal for measuring the first component to the device for measuring the first component. In addition, the communication interface 615 may transmit a result of estimating the second component to the external device or receive various items of reference information from the external device.

Figure 6C:
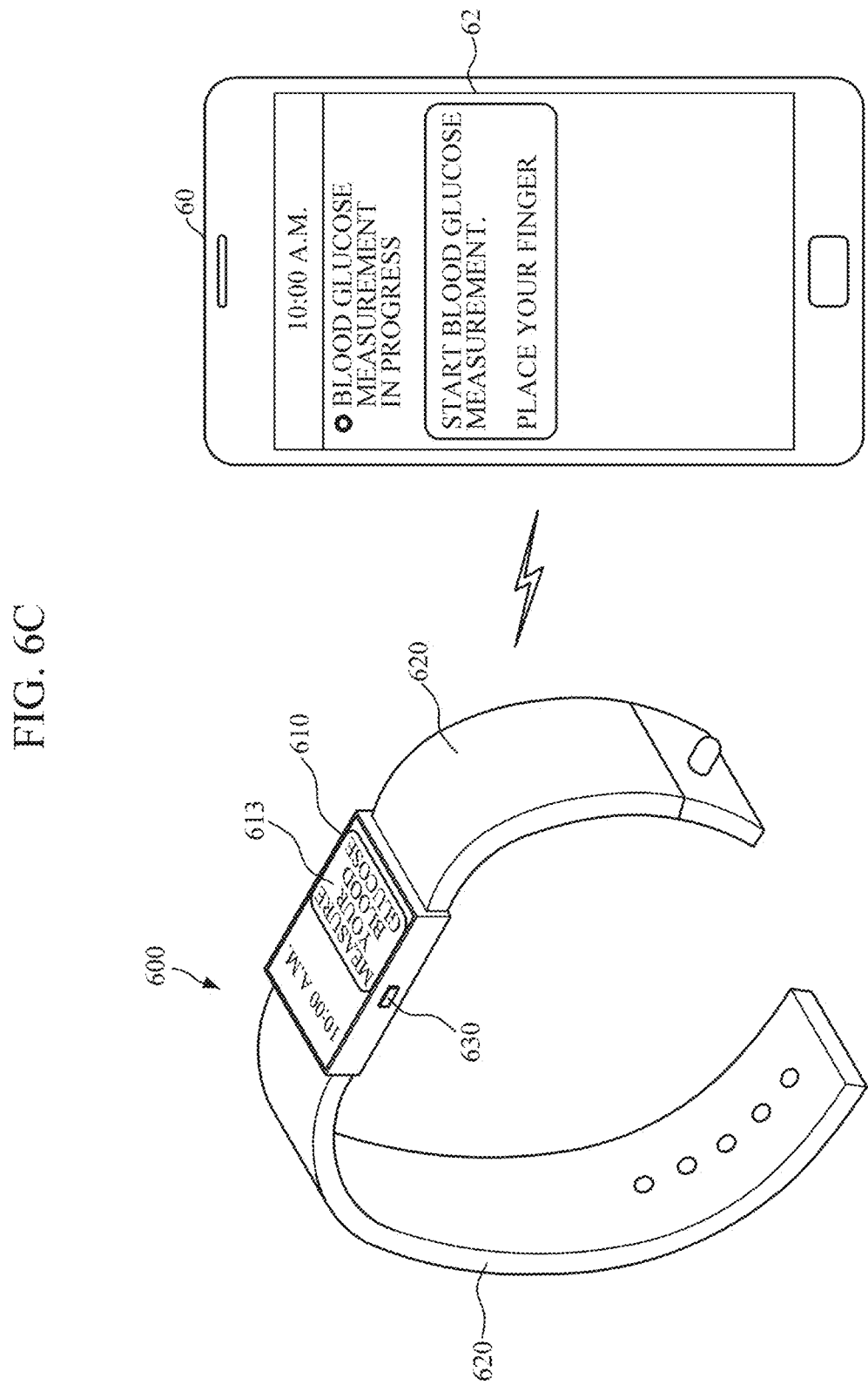
FIG. 6C is a diagram illustrating an example in which the electronic device of FIGS. 6A and 6B guides the measurement of a target component.

FIG. 6C is a diagram illustrating one embodiment of the electronic devices 600a and 600b in accordance with the embodiments of FIGS. 6A and 6B. Referring to FIG. 6C, the electronic devices 600a and 600b may be implemented as a wearable device 600 worn on a wrist of a user. The wearable device 600 may continuously measure a pulse wave signal while being worn on the wrist of the user, thereby continuously estimating blood glucose and guiding the blood glucose measurement of a blood glucose measurement device. In addition, the blood glucose measurement device may be a smartphone 60 including a function of non-invasively measuring blood glucose, but is not limited thereto. However, the electronic devices are not limited to the example shown in FIG. 6C, and the opposite case is possible. As described above, the electronic devices may be other various types of devices.

The wearable device 600 includes a main body 610 and a strap 620, and the strap 620 may be formed to be flexible. The strap 620 may be bent to wrap around the wrist of the user and may be configured in the form separated from the user's wrist or in the form of a non-separable band. In this case, the strap 620 may be filled with air or have an air bag to have elasticity according to a change in pressure applied to the wrist and may transmit the pressure change of the wrist to the main body 610.

Various configurations according to the embodiments of FIGS. 6A and 6b may be mounted in the main body 610. For example, the pulse wave measurer 611 may be mounted in such a manner that at least a part of the pulse wave measurer 611 is exposed to a rear surface of the main body 610 so as to be in contact with an upper part of the wrist. In addition, the processor 612 which estimates blood pressure and guides the user to measure blood glucose based on the pulse wave signal is mounted in the main body 610 and may be electrically connected to the pulse wave measurer 611 to receive the pulse wave signal. Moreover, the contact pressure measurer 616 may be disposed behind the pulse wave measurer 611 in the main body 610 and may measure a contact pressure when an object of interest is in contact with the pulse wave measurer 611. The storage 614 and the communication interface 615 are mounted on the main body 610 and the output interface 613 may be mounted on a front surface of the main body 610.

Further, a battery for supplying power to the wearable device may be embedded in the main body 610 or the strap 620.

When a blood glucose measurement event occurs, the processor 612 may output guide information, such as "Please measure your blood glucose level," through the output interface 613. The user may directly drive the smartphone 60 equipped with a blood glucose measurement function according to the guide, or may measure blood glucose by directly driving an invasive or minimally invasive blood glucose measurement sensor. Alternatively, when the communication interface 615 has already been connected to the smartphone 60 via Bluetooth or the like, the processor 612 may transmit a control signal for controlling the blood glucose measurement function of the smartphone 60, as well as output the guide information.

The smartphone 60 may guide the user to initiate blood glucose measurement by outputting information, such as "Start measuring your blood glucose. Please place your finger," to the display 62. At this time, vibration or an acoustic signal may be output together. When the blood glucose measurement is completed, the smartphone 60 may output a blood glucose measurement result to the display 62. In addition, the smartphone 60 may transmit the blood glucose measurement result to the wearable device 600.

The smartphone 60 may include a sensor configured to measure a spectrum from the user using Raman spectroscopy, near-infrared/mid-infrared spectroscopy, or the like. The sensor may include a light source configured to emit light to the object of interest of the user and a detector configured to detect light reflected or scattered from the object of interest. In addition, the sensor may include a spectroscopic module configured to acquire a spectrum by spectroscopically analyzing the reflected or scattered light. When the user brings the object of interest in contact with a spectrum measurement sensor, the smartphone 60 may acquire a spectrum from the object and estimate blood glucose by analyzing the acquired spectrum. A variety of known techniques may be used as the method of measuring the blood glucose through spectrum analysis.

Figure 7:
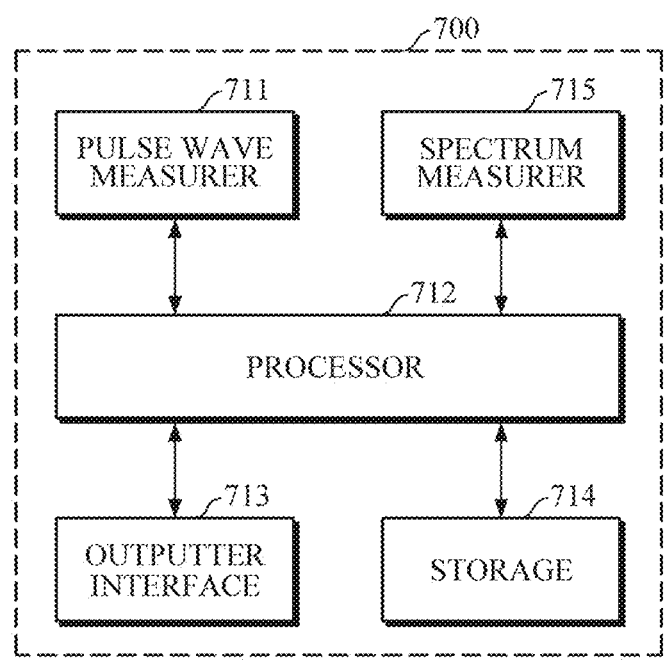
FIG. 7 is a block diagram illustrating an electronic device according to another embodiment.

FIG. 7 is a block diagram illustrating an electronic device according to another embodiment. The electronic device 700 may be a portable terminal, such as a smartphone, a tablet PC, a notebook PC, a wearable device, or the like, but is not limited thereto. For example, the electronic device 700 may monitor an occurrence of a blood glucose estimation event while continuously estimating blood pressure using a pulse wave signal, and may estimate blood glucose when necessary.

Referring to FIG. 7, the electronic device 700 may include a pulse wave measurer 711, a processor 712, an output interface 713, a storage 714, and a spectrum measurer 715. The pulse wave measurer 711 and the spectrum measurer 715 may be realized as a spectrometer.

The pulse wave measurer 711 may measure a pulse wave signal including a PPG signal from an object of interest. The pulse wave measurer 711 may include a light source and a detector. The light source may be formed of a light emitting diode (LED), a laser diode (LD), or a phosphor, but is not limited thereto. The light source may be formed as one or two or more arrays, and each light source may emit light of a different wavelength. The detector may be formed of one or more pixels and each pixel may include a photodiode or a PTr which receives light scattered or reflected from an object of interest irradiated by the light source.

When the pulse wave signal is measured, the processor 712 may estimate a second component, such as blood pressure, based on the pulse wave signal and/or a contact pressure. As described above, the second component may be measured based on an oscillometric method based on the pulse wave signal and the contact pressure. However, the embodiment is not limited thereto and various other known techniques may be used.

In addition, when the pulse wave signal is measured, the processor 712 may acquire physiological information to monitor a measurement event of a first component, such as blood glucose, based on the pulse wave signal. The processor 712 may estimate PRV through analysis of RR periods of the pulse wave signal and monitor the measurement event of the first component through analysis of the PRV. For example, the processor 712 may extract time domain features and/or frequency domain features by analyzing the PRV in time domain and/or frequency domain, and monitor the occurrence of the measurement event of the first component based on the extracted feature value. Alternatively, the processor 712 may monitor the measurement event of the first component based on a change in a tachogram pattern of the extracted PRV relative to a tachogram pattern of PRV at a reference point in time.

When the measurement event of the first component occurs, the processor 712 may control the spectrum measurer 715 to measure a spectrum from the object of interest of the user. The spectrum measurer 715 may acquire the spectrum using one of near-infrared spectroscopy, mid-infrared spectroscopy, and Raman spectroscopy. In addition, the processor 712 may estimate the first component, such as blood glucose, through a spectrum analysis using various known techniques.

When the first component measurement event occurs, the processor 712 may control the spectrum measurer 715 and guide the user to measure the first component through the output interface 713. For example, the processor 712 may provide guide information related to a contact position or a contact pressure of the spectrum measurer 715.

The output interface 713 may output an estimation result of the first component, an estimation result of the second component, a variety of guide information generated by the processor 712 regarding measurement of the first component, and the like.

Various items of reference information required for estimating the first component and/or estimating the second component, the pulse wave signal measured by the pulse wave measurer 611, a processing result of the processor 612, and the like may be stored in the storage 614. For example, the reference information may include a threshold used for determining whether a first component estimation event has occurred, a type and a calculation method of a feature to be extracted, and a first component estimation event determination period. In addition, the reference information may include an estimation model and the estimation timing for estimating the second component. Further, the storage 614 may store user characteristic information, such as a health status of the user.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for health care, the apparatus comprising:
   a physiological information acquirer configured to acquire physiological information related to a target component of a user, the physiological information comprising at least one of a heart rate variability (HRV) and a pulse rate variability (PRV); and
   a processor configured to extract a feature value from the physiological information, and based on a change in the extracted feature value, relative to a feature value at a reference point in time, being outside a predetermined normal range, perform an operation to guide the user on a time to measure the target component,
   wherein the processor is further configured to:
   transform the at least one of the HRV and the PRV in a time domain into a frequency domain and extract, as feature values, power in low frequency range (LF) and power in high frequency range (HF),
   determine that a hypoglycemia event occurs based on the LF being outside a first predetermined normal range, and determine that a hyperglycemia event occurs based on the HF being outside a second predetermined normal range, and
   output, to the user, different recommendation information on an action to be taken based on whether an occurrence of the hyperglycemia event or the hypoglycemia event is determined.

2. The apparatus of claim 1, wherein the physiological information further comprises at least one of heart rate, pulse rate, blood flow, viscosity, hematocrit, respiration, skin temperature, and moisture.

3. The apparatus of claim 1, wherein the processor is configured to extract one or more feature values from the physiological information based on a characteristic of the user.

4. The apparatus of claim 1, wherein the processor is further configured to monitor the change in the extracted feature value based on a change in a tachogram pattern of the HRV or the PRV of the physiological information.

5. The apparatus of claim 1, wherein the processor is further configured to extract, as the feature value, an LF/HF ratio, and determine a glucose metabolic abnormality based on a change in the LF/HF ratio during a predetermined time period being greater than a threshold value.

6. The apparatus of claim 1, wherein, based on the change in the extracted feature value being outside the predetermined normal range, the processor is further configured to generate at least one of information for guiding the user to measure the target component through a target component measurement sensor and a control signal for controlling the target component measurement sensor.

7. The apparatus of claim 6, wherein the processor is further configured to receive a result of measuring the target component from the target component measurement sensor and generate information for guiding health care of the user based on the result of measuring the target component.

8. The apparatus of claim 1, wherein the target component includes one or more of blood glucose, cholesterol, triglyceride, protein, and uric acid.

9. A method for health care, the method comprising:
   acquiring physiological information related to a target component of a user, the physiological information comprising at least one of a heart rate variability (HRV) and a pulse rate variability (PRV);
   extracting a feature value from the physiological information; and
   performing an operation to guide the user on a time to measure the target component, based on a change in the extracted feature value, relative to a feature value at a reference point in time, being outside a predetermined normal range,
   wherein the extracting comprises transforming the at least one of the HRV and the PRV in a time domain into a frequency domain and extracting, as feature values, power in low frequency range (LF) and power in high frequency range (HF), and
   wherein the method further comprises:
   determining that a hypoglycemia event occurs based on the LF being outside a first predetermined normal range, and determining that a hyperglycemia event occurs based on the HF being outside a second predetermined normal range; and
   outputting, to the user, different recommendation information on an action to be taken based on whether an occurrence of the hyperglycemia event or the hypoglycemia event is determined.

10. The method of claim 9, wherein the extracting comprises extracting one or more feature values from the physiological information based on a characteristic of the user.

11. The method of claim 9, further comprising:
    monitoring the change in the extracted feature value based on a change in a tachogram pattern of the HRV or the PRV of the physiological information.

12. The method of claim 9, wherein the guiding the user on the time to measure the target component comprises, in response to the extracted feature value being outside the predetermined normal range, generating information for guiding the user to measure the target component through a target component measurement sensor and outputting the generated information to the user.

13. The method of claim 9, wherein the guiding the user on the time to measure the target component comprises, in response to the extracted feature value being outside the predetermined normal range, generating a control signal for controlling a target component measurement apparatus and transmitting the generated control signal to the target component measurement apparatus.

14. The method of claim 9, further comprising:
    when the target component is measured by a target component measurement apparatus, receiving a measurement result of the target component from the target component measurement apparatus;
    generating information for guiding health care of the user based on the measurement result received from the target component measurement apparatus; and outputting at least one of the measurement result received from the target component measurement apparatus and the information for guiding the health care of the user.

15. An electronic device comprising:
a pulse wave measurer configured to measure a pulse wave signal from a user; and
a processor configured to acquire physiological information related to a first component of the user based on the pulse wave signal, extract a feature value from the physiological information, and based on a change in the extracted feature value, relative to a feature value at a reference point in time, being outside a predetermined normal range, perform an operation to guide the user on a time to measure the first component,
wherein the physiological information comprises at least one of a heart rate variability (HRV) and a pulse rate variability (PRV), and
wherein the processor is further configured to:
transform the at least one of the HRV and the PRV in a time domain into a frequency domain and extract, as feature values, power in low frequency range (LF) and power in high frequency range (HF),
determine that a hypoglycemia event occurs based on the LF being outside a first predetermined normal range, and determine that a hyperglycemia event occurs based on the HF being outside a second predetermined normal range, and
output, to the user, different recommendation information on an action to be taken based on whether an occurrence of the hyperglycemia event or the hypoglycemia event is determined.

16. The electronic device of claim 15, wherein the pulse wave measurer comprises one or more light sources configured to emit light to the user and one or more detectors configured to detect light scattered or reflected from the user.

17. The electronic device of claim 15, wherein the processor is further configured to estimate, based on the pulse wave signal, a second component that includes one or more of blood pressure, vascular age, a degree of arteriosclerosis, aortic pressure waveform, vascular compliance, stress index, and a degree of fatigue.

18. The electronic device of claim 17, further comprising:
a contact pressure measurer configured to a contact pressure between the user and the pulse wave measurer when the user is in contact with the pulse wave measurer,
wherein the processor is further configured to estimate the second component based on the pulse wave signal and the contact pressure.

19. The electronic device of claim 15, wherein the processor is further configured to estimate the PRV based on the pulse wave signal and monitor the change in the extracted feature value based on the estimated PRV.

20. The electronic device of claim 19, wherein the processor is further configured to acquire a tachogram of the PRV pulse rate variability and monitor the change in the extracted feature value based on a change in a pattern of the tachogram.

21. The electronic device of claim 15, further comprising an output interface configured to, in response to the extracted feature value being outside the predetermined normal range, output information for guiding the user on the time to measure the first component.

22. The electronic device of claim 15, further comprising a communication interface configured to, in response to the extracted feature value being outside the predetermined normal range, transmit a control signal for controlling a measurement of the first component to an external device.

23. The electronic device of claim 22, wherein the first component includes at least one of blood glucose, cholesterol, triglyceride, protein, and uric acid and the external device includes a device that measures the first component in a non-invasive manner.

24. The electronic device of claim 15, further comprising:
a spectrum measurer configured to measure a spectrum for estimating the first component from the user,
wherein the processor is further configured to monitor the spectrum, and determine a value of the first component based on the physiological information and the spectrum.

25. The electronic device of claim 24, wherein the spectrum measurer is configured to measure the spectrum using at least one of near-infrared spectroscopy, mid-infrared spectroscopy, and Raman spectroscopy.

* * * * *